(12) United States Patent
Emken et al.

(10) Patent No.: US 11,119,337 B1
(45) Date of Patent: Sep. 14, 2021

(54) OPHTHALMIC DEVICE INCLUDING OPTICAL ELEMENTS HAVING PATTERNED TABS

(71) Applicant: Verily Life Sciences LLC, Mountain View, CA (US)

(72) Inventors: Jeremy L. Emken, Belmont, CA (US); Scott B. Kennedy, Mountain View, CA (US)

(73) Assignee: Verily Life Sciences LLC

(*) Notice: Subject to any disclaimer, the term of this patent is extended or adjusted under 35 U.S.C. 154(b) by 354 days.

(21) Appl. No.: 15/702,297

(22) Filed: Sep. 12, 2017

Related U.S. Application Data

(60) Provisional application No. 62/402,734, filed on Sep. 30, 2016.

(51) Int. Cl.
  *G02C 7/04* (2006.01)
  *G02C 11/00* (2006.01)
  *A61F 2/16* (2006.01)

(52) U.S. Cl.
  CPC .......... *G02C 7/049* (2013.01); *G02C 7/041* (2013.01); *G02C 11/10* (2013.01); *A61F 2/1635* (2013.01); *G02C 2202/16* (2013.01)

(58) Field of Classification Search
  CPC combination set(s) only.
  See application file for complete search history.

(56) References Cited

U.S. PATENT DOCUMENTS

| | | | |
|---|---|---|---|
| 6,991,651 B2 | 1/2006 | Portney | |
| 8,906,088 B2 | 12/2014 | Pugh et al. | |
| 9,044,200 B1 | 6/2015 | Liu et al. | |
| 2008/0208335 A1 | 8/2008 | Blum et al. | |
| 2012/0245444 A1 | 9/2012 | Otis et al. | |
| 2012/0300171 A1 | 11/2012 | Gupta et al. | |
| 2013/0245754 A1 | 9/2013 | Blum et al. | |
| 2014/0253870 A1 | 9/2014 | Jiang et al. | |
| 2015/0077662 A1* | 3/2015 | Pugh | G02C 7/049 349/13 |
| 2015/0214567 A1* | 7/2015 | Etzkorn | H01M 2/0202 429/303 |
| 2015/0362752 A1* | 12/2015 | Linhardt | G02C 7/04 349/13 |

* cited by examiner

*Primary Examiner* — Lauren Nguyen
(74) *Attorney, Agent, or Firm* — Christensen O'Connor Johnson Kindness PLLC

(57) ABSTRACT

An ophthalmic device including patterned tabs is disclosed herein. An example ophthalmic device may include a plurality of optical elements formed into a stack and a substrate. A subset of optical elements of the plurality of optical elements may include a tab extending radially outward from an edge perimeter of a respective optical element, and each tab may include an opening formed there through. The substrate may include a plurality of bond pads, where each optical element of the plurality of optical elements is coupled to one of the plurality of bond pads by a conductive material, and the conductive material is disposed within respective openings of the subset of optical elements of the plurality of optical elements.

26 Claims, 6 Drawing Sheets

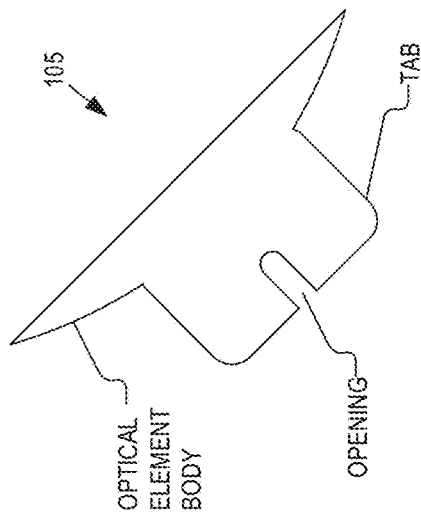
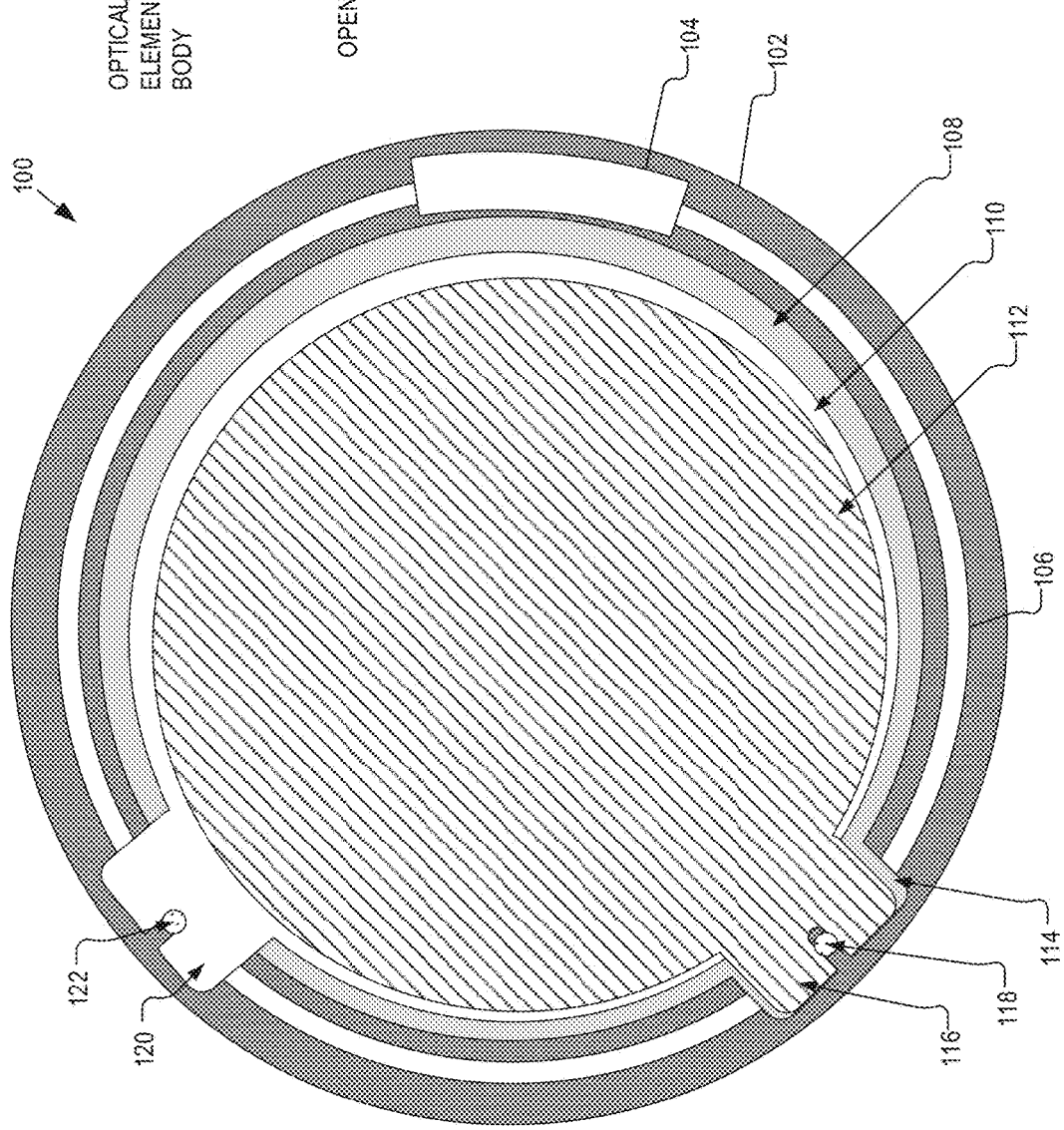

OPHTHALMIC DEVICE INCLUDING OPTICAL ELEMENTS HAVING PATTERNED TABS

CROSS REFERENCE TO RELATED APPLICATIONS

This application claims the benefit of U.S. Provisional Application No. 62/402,734 filed on Sep. 30, 2016, the contents of which are incorporated herein by reference.

TECHNICAL FIELD

This disclosure relates generally to ophthalmic devices, and in particular but not exclusively, relates to ophthalmic devices including patterned tab features.

BACKGROUND INFORMATION

The evolution of ophthalmic devices has seen the introduction of circuits, sensors, actuators, and the like into eye-mountable and implantable lenses. Such devices may be "smart" in the sense that they may offer various optical and/or medical benefits, such as vision correction, accommodation, medical monitoring, and the like. The introduction of the circuits, sensors, actuators, etc., has been accompanied with the requirement of interconnecting these components using electrical traces and solder-like substances to complete the circuits. However, the coupling of the various components using solder-like substances may create cosmetically undesirable connections. As such, it may be desirable to include features on various components of the ophthalmic device that remedy any cosmetically undesirable interconnections, and which may not interfere with a user's vision.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 1A is a plan view illustration of an ophthalmic device including patterned tabs in accordance with an embodiment of the present disclosure.

FIG. 1B is a plan view of an illustration of a tab in accordance with an embodiment of the present disclosure.

DETAILED DESCRIPTION

Figure 1D:
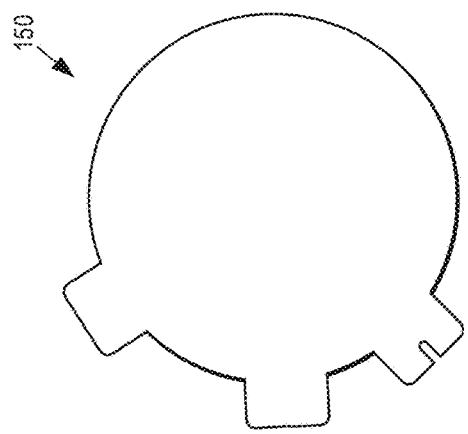
FIG. 1D is an example of an optical element in accordance with an embodiment of the present disclosure.

Embodiments of a system and method for the alignment of conductive medium based on patterned tab features are described herein. For example, openings formed in tabs of optical elements may provide alignment of the conductive medium when bonding the optical elements to one or more bond pads. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

FIG. 1A is a plan view illustration of an ophthalmic device 100 including patterned tabs in accordance with an embodiment of the present disclosure. The ophthalmic device 100 may be an on-eye device, such as a contact lens or a smart contact lens. In some embodiments, the ophthalmic device 100 may include electronics and various interconnections to control a dynamic optic. For example, control electronics may control a dynamic optic to provide accommodation for a user. The dynamic optic may be formed from a stack of optical elements, each receiving a voltage, for example, to modulate the dynamic optic. The interconnections to the optical elements may be provided in features of the optical elements. For example, one or more of the optical elements may include a tab that has an opening, e.g., a via, formed there through. The opening(s) may provide for alignment of the optical elements, and further provide a cavity for the placement of the material used to form at least a part of the interconnections.

The illustrated embodiment of the ophthalmic device 100 includes a substrate 102, and first, second, and third optical elements 108, 110, and 112, respectively. In some embodiments, the first, second, and third optical elements 108-112 may be formed into a stack, and each may include at least one patterned tab, such as tabs 114, 120, and 116, respectively, and possibly additional tabs. In some embodiments, the ophthalmic device 100 may further include a soft over mold disposed around the substrate 102 and the first, second, and third optical elements 108-112. The soft over mold, which may also be referred to as an encasement, may provide protection to the combination of the substrate 102 and the three optical elements 108-112, and may be formed from biocompatible materials, for example. While the ophthalmic device 100 may be discussed as having three optical elements, the number of optical elements is a non-limiting aspect of the present disclosure, and other numbers of optical elements are within the scope of the present disclosure. For example, the number of optical elements could be one, two, three, four, five, and so on.

In some embodiments, the substrate 102 may encircle at least some of the first, second, and third optical elements 108-112. For example, the substrate 102 may be toroidal-shaped, and may have an inner diameter that encompasses at least part of the first, second, and third optical elements 108-112. In some embodiments, the substrate 102 may encompass all but the tabs of the first, second, and third optical elements 108-112. In other embodiments, the substrate 102 may encompass at least some of the second and third optical elements 110 and 112, but rest upon an outer area of the first optical element 108. The substrate 102 may provide structural support for control electronics 104, interconnect 106 and various bond pads (not shown in FIG. 1, but see FIGS. 2A, 2B, 2C and 3 for examples). The substrate 102 may further provide structural support for one or more antennae (not shown), which may be formed in one or more loops around the substrate 102, for example.

The first optical element 108 may have an optical element body and a patterned tab 114. In some embodiments, the first optical elements 108 may include more than one tab with at least one of the tabs being patterned. The optical element body may have a hemi-spherical shell shape, which may appear disc-shaped in FIG. 1A. In some embodiments, the first optical element 108 may have a diameter ranging from 10 to 13 mm. The first optical element may be formed from a rigid or semi-rigid material, for example. The tab 114 may have an opening (see FIG. 1B for one example opening) formed there through, where the opening may be referred to as the patterned feature of the tab. The first optical element 108 may further include one or more conductors (see FIGS. 2A and 2B), and one or more transparent or semi-transparent conductors (not shown). For example, the one or more conductors may be disposed on a sidewall of the opening and on one or more sides of the tab 114 and/or the body of the optical element 108. The transparent or semi-transparent conductor may be disposed in a central region of the body of the optical element 108. The central region may coincide with an optical area of the ophthalmic device 100, for example, and may be about 8 mm in diameter and centered on an optical axis of the ophthalmic device 100. The one or more conductors may be coupled to the transparent or semi-transparent conductor to provide a conductive path to provide a voltage to the transparent or semi-transparent conductor, for example.

FIG. 1B is a plan view of an illustration of a tab 105 in accordance with an embodiment of the present disclosure. The tab 105 may be just one example of the tabs 114, 116, and/or 120. The tab may extend radially outward from a perimeter edge of the optical element body, for example. In some embodiments, the tab may be 0.5 to 3 mm in length in the radial direction and 2 to 4 mm in length in an axial direction. The opening may be a slot as shown, or it may be any other type of opening, such as a hole, for example. In embodiments where the opening is a slot, the radial length of the slot may depend on the position of a bond pad of the substrate 102 to an outer edge of the tab, for example. The width of the slot may be from 300 to 600 microns, for example. In embodiments where the opening is a hole, the diameter of the hole may be similarly sized, e.g., 300 to 600 microns. In general, the size of the opening may be based on an amount of conductive material dispensed during fabrication and the size of the underlying bond pads. It may be desirable to size the opening to provide room to hold the dispensed conductive material, for example. While the tab is depicted as a rectangular-like shape extension of the optical element body, other shapes are contemplated, such as half-circles, half-ovals, triangles, etc. As such, the shape and size of the tab is a non-limiting aspect of the present disclosure. In some embodiments, however, one or more of the optical elements 108-112 may not have a tab, but an opening may be formed through the optical element at a peripheral location, for example. Alternatively, each of the optical elements 108-112 may have a plurality of tabs, with a subset of the plurality of tabs including the opening. For example, one tab may include the opening, either a slit or a hole, and the other tabs may not include an opening. The number of tabs, however, should not be considered limiting, and any number of tabs is within the scope of the present disclosure.

Referring back to FIG. 1A, the opening in the tab 114 may provide an alignment feature for aligning the first optical element 108 to a bond pad disposed on or a via formed through the substrate 102, for example. Additionally, the opening may provide a space where conductive material may wick into during fabrication of the ophthalmic device 100. The wicking of the conductive material may promote a cleaner, e.g., more cosmetically appealing, application of the conductive material, and the opening may further provide a location for the application of the conductive material during fabrication. Additionally, the openings in the tab 114 may provide an alignment marker during fabrication of the ophthalmic device 100. While the tab 114 is shown to be on top of the substrate 102, the tab 114 may alternatively be disposed below the substrate 102. The depiction of FIG. 1A is for illustrative purposes and should not be considered limiting.

The second and third optical elements 110 and 112, respectively, may be similar to the first optical element 108, but may differ with respect to locations of the one or more conductors and the transparent or semi-transparent conductors. The second and third optical elements may also have patterned tabs, such as tabs 120 and 116, respectively. In some embodiments, both the second and third optical elements 110,112 may have more than one tab with at least one of the tabs being patterned. Additionally, the second and third optical elements 110 and 112 may be formed from the same or like material as the first optical element 108.

The first, second, and third optical elements 108, 110, and 112, respectively, may be formed into a stack, for example. In some embodiments, the first optical element 108 may be a posterior optical element, which may be eye-facing when the ophthalmic device 100 is worn by a user. The second optical element 110 may be a middle optical element disposed between the first and third optical elements 108 and 112, respectively. Further, the third optical element may be an anterior optical element, which may be external facing when the ophthalmic device 100 is worn by a user. The stack may be at least partially ringed by the substrate 102, which may include at least two bond pads for electrically coupling to the first, second, and third optical elements 108-112. In some embodiments, the first and third optical elements 108 and 112 may be coupled to the same bond pad via conductive material 118, whereas the second optical element 110 may be coupled to a different bond pad via conductive material 122. The conductive materials 118 and 122 may be formed from the same or different conductive materials. In some embodiments, the conductive materials 118 and 122 may be a conductive epoxy or silver paste.

During fabrication of the ophthalmic device 100, the openings in the tabs 114 and 116 of the first and third optical elements 108, 112 may be aligned. In turn, the aligned openings may also be aligned to the bond pad disposed on or a via through the substrate 102. In some embodiments, the first and third optical elements 108, 112 may be disposed on opposing sides of the substrate 102. In some embodiments, the first and third optical elements 108. 112 may be disposed on a same side of the substrate 102, such as an anterior or posterior side. Post alignment of the openings, the conductive material 118 may be dispensed into the openings of the tabs 114 and 116. Sidewalls of the openings in the tabs 114 and 116 may have a conductor disposed thereon, which may be electrically coupled to the conductive material 118. The conductive material 118 may then be cured, e.g., heated, UV exposure, etc. As a result, the first and third optical elements may be electrically coupled to the control electronics 104 via the conductive material 118, the underlying bond pad, and the interconnect 106.

Further, the ophthalmic device 100 may include liquid crystal (LC) material between adjacent ones of the first, second, and third optical elements 108-112. For example, LC material may be disposed between the first and second optical elements 108 and 110, and also disposed between the second and third optical elements 110 and 112. In some embodiments, the LC material may be disposed at least within the optical area of the ophthalmic device 100.

To actuate the LC material, the transparent or semi-transparent conductors disposed on the three optical elements 108, 110, and 112 may be charged with a voltage. As a result, a potential difference may form across the LC material between the adjacent optical elements. The potential difference may cause the LC materials to orient parallel or perpendicular to the optical axis of the ophthalmic device 100, which may affect the optical properties of the ophthalmic device 100. For example, the ophthalmic device may provide accommodation to the user due to a change in the orientation of the LC materials.

The first, second and third optical elements 108-112 are shown in FIG. 1A as having different diameters. Similarly, the tabs 114 and 116 are shown as having different axial lengths. These differences, however, are included to more clearly illustrate various aspects of the disclosure, and should not be considered limiting. In some embodiments, the sizes of the various tabs may be similar, but in other embodiments, the sizes of the tabs may be different in both axial length and radial width. Further, while the tabs are shown as rectangles extending out of the optical elements, the shape of the tab is a non-limiting aspect as well, and all shapes are contemplated. Additionally, the three optical elements may each have multiple tabs or no tabs at all, but may still include the openings for providing interconnection paths between the various optical elements and the substrate 102, for example. In some embodiments, however, one or more of the optical elements 108-112 may not include an opening and/or a tab.

Figure 1C:
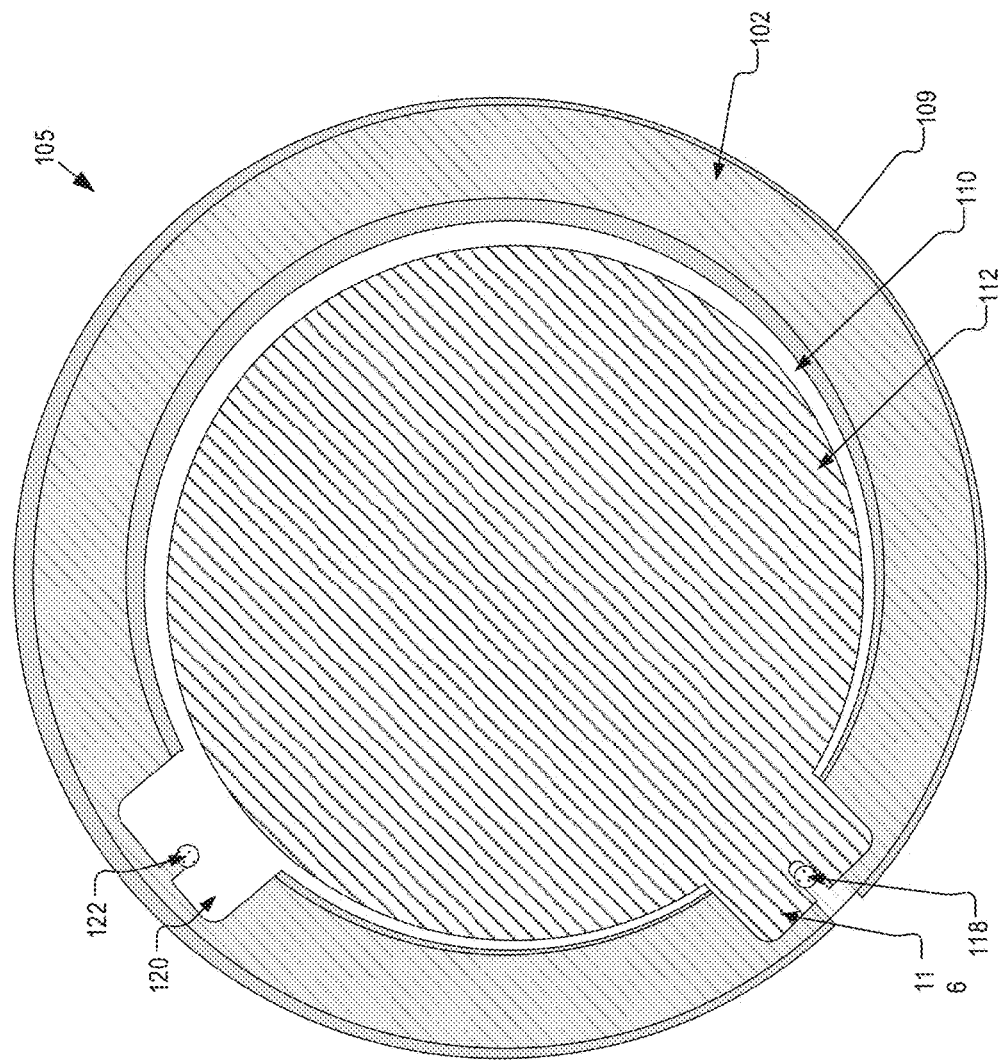
FIG. 1C is a plan view illustration of an ophthalmic device including patterned tabs in accordance with an embodiment of the present disclosure.

FIG. 1C is a plan view illustration of an ophthalmic device 105 including patterned tabs in accordance with an embodiment of the present disclosure. the ophthalmic device 105 may be similar to the ophthalmic device 100 except for the posterior optical element. For example, the posterior optical element 108 of the ophthalmic device 100 includes a tab 114, whereas the posterior optical element 109 of the ophthalmic device 105 does not include a tab. Additionally, the posterior optical element 109 may not include an opening, but may include a patterned bond pad instead. Outside of the difference in the posterior optical elements, the ophthalmic device 105 and 100 may be substantially similar. However, some of the features of ophthalmic device 100 have been omitted in FIG. 1C so not to obscure the differences. For example, the control electronics 104 and interconnect 106 have been omitted in FIG. 1C.

The illustrated embodiment of the ophthalmic device 105 includes the substrate 102, and three optical elements 109, 110, and 112. Optical elements 110 and 112 include respective tabs 120 and 116. However, optical element 109 does not include a tab. Instead, a diameter of the optical element 109 is such as to at least coincide with the tab 116 of the optical element 112. Additionally, the optical element 109 may have a diameter that is the same or greater than the substrate 102. In some embodiments, the substrate 102 may rest upon the perimeter of the first optical element 109.

In some embodiments, an opening may be formed through the optical element 109 at a peripheral location, for example. The opening may be formed so to align with a bond pad of or an opening, e.g., via, formed through the substrate 102 and/or the opening in the tab 116, for example. In some embodiments, however, the optical element 109 may not include an opening, but instead may have a bond pad formed at a perimeter location to align with an opening formed in the substrate 102, which may also be aligned to the opening in the tab 116.

The substrate 102 may be disposed between a perimeter of the optical element 109 and at least the tab 116 of the optical element 112. The opening in and/or the bond pad of the optical element 109 and the opening in the tab 116 may both be aligned to the bond pad 118 of the substrate 102. In some embodiments, the bond pad 118 may be formed through the opening in the substrate 102 so that both the optical elements 109 and 112 may be coupled to the bond pad 118 with a conductive material, e.g., silver epoxy.

While the diameters of the optical elements 109-112 may be shown as different, and their relative center axes displaced, the depiction should not be considered limiting and is depicted as such to better illustrate the various components.

FIG. 1D is an example of an optical element 150 in accordance with an embodiment of the present disclosure. The optical element 150 may be one example of the optical elements 108, 110, and 112. However, the optical element 150 includes a plurality of tabs with at least one of the tabs being patterned, e.g., including an opening. As discussed above, the patterned tab may be used for electrically coupling to a substrate and/or another tab. The non-patterned tabs, however, may be used for manipulating and/or aligning the optical element 150 during fabrication of an ophthalmic device. Although three tabs are shown in FIG. 1D, any number of tabs, such as four or five, may be implemented.

Figure 2A:
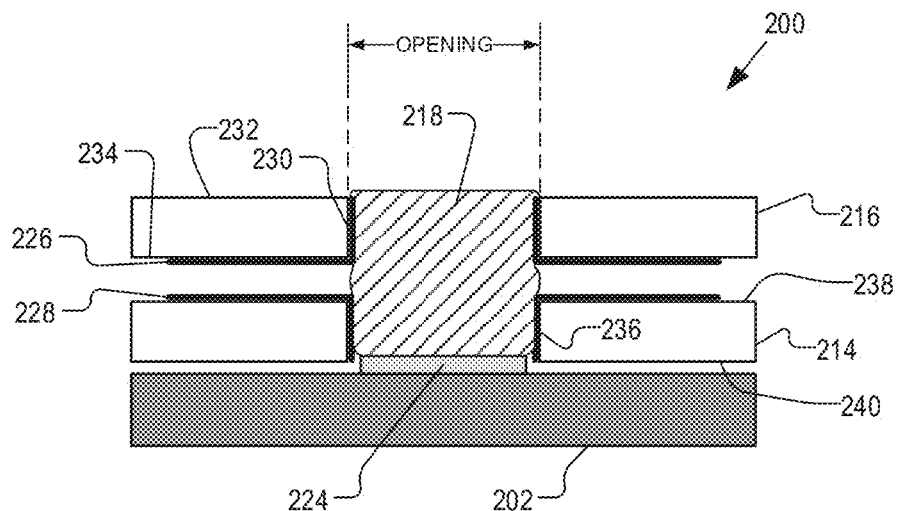
FIG. 2A is an example cross-sectional view of an ophthalmic device including patterned tabs in accordance with an embodiment of the present disclosure.

FIG. 2A is an example cross-sectional view of an ophthalmic device 200 including patterned tabs in accordance with an embodiment of the present disclosure. FIG. 2A may be an example of the ophthalmic devices 100 and/or 105. The illustrated embodiment of the ophthalmic device 200 includes a substrate 202, tabs 214 and 216, and conductive material 218. The conductive material 218 may electrically couple the conductors 226, 228 to bond pad 224, for example.

The tabs 214 and 216 may be examples of tabs 114 and 116, respectively, and may be extensions of associated optical elements, such as the optical elements 208 and 212. The illustrated embodiment of the tab 214 includes an opening having a sidewall 236. The tab 214 may have a posterior side 240 and an anterior side 238. A conductor 228 may be disposed on the sidewall 236 and at least the anterior side 238. Similarly, the illustrated embodiment of the tab 216 includes an opening have a sidewall 230, and the tab 216 may further have a posterior side 234 and an anterior side 232. A conductor 226 may be disposed on the sidewall 230 and at least the posterior side 234. The conductors 226 and 228 may be formed from one or more metals deposited on the various surfaces of the tabs 214 and 216. For example, the conductors 226 and 228 may be formed from titanium and gold. Alternatively, the conductors 226 and 228 may be formed from silver or aluminum. The conductors 226 and 228 may be coupled to respective transparent or semi-transparent conductors disposed in an optical area of associated optical elements.

The illustrated embodiment of the substrate 202 includes a bond pad 224. The bond pad 224 may be coupled to control electronics via one or more interconnects (not shown). For example, the bond pad 224 may be coupled to the control electronics 104 via interconnect 106. In some embodiments, the bond pad 224 may be formed from titanium and gold or aluminum. The bond pad may provide a surface to which the conductive material 218 may adhere and electrically couple.

The optical elements 214 and 216 may be in a stack with the substrate 202. In some embodiments, the optical element 214 may be disposed between the substrate 202 and the optical element 216. For example, an anterior side of the substrate 202 may be adjacent to the posterior side 240 of the tab 214, and the anterior side of the tab 214 may be adjacent to the posterior side of the tab 216. While the ophthalmic device 200 may have an additional optical element, such as the second optical element 110, the additional optical element is not shown in FIG. 2A because a tab of the additional optical element may not be oriented to coincide with the tabs 214 and 216. However, the additional optical element may be disposed between the optical elements associated with the tabs 214 and 216, similar to the optical element 110.

The conductive material 218 may be disposed within the opening of the first and third tabs 214 and 216, and further disposed on the bond pad 224. The conductive material 218 may be a conductive epoxy or silver paste, for example. In some embodiments, the conductive material 218 may be dispensed, by jet dispense for example, during fabrication of the ophthalmic device 200. For example, the openings in both the tabs 214 and 216 may be aligned to one another and positioned over the bond pad 224 before the conductive material 218 is dispensed within the openings. The conductive material 218 may be subsequently cured, such as by heat or UV exposure.

Figure 2B:
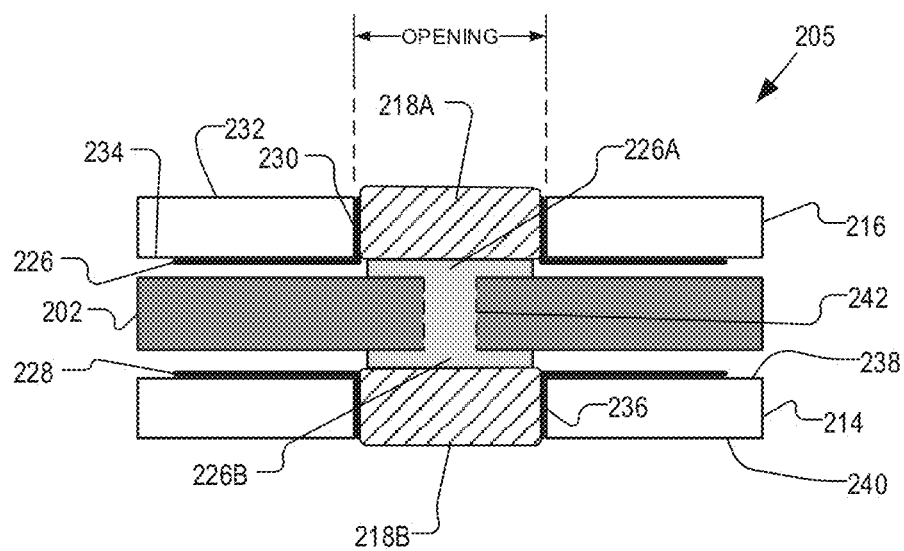
FIG. 2B is a cross-sectional view of an ophthalmic device including patterned tabs in accordance with an embodiment of the present disclosure.

FIG. 2B is a cross-sectional view of an ophthalmic device 205 including patterned tabs in accordance with an embodiment of the present disclosure. The ophthalmic device 205 may be an example of the ophthalmic devices 100 and/or 105. Additionally, the ophthalmic device 205 may be similar to the ophthalmic device 200 except for a change in relation of the substrate 202 to the tabs 214 and 216. Specifically, the substrate 202 of the ophthalmic device 205 is disposed between the tabs 214 and 216 instead of adjacent to the tab 214.

The illustrated embodiment of the substrate 202 may have a via 242 formed through it, which may include a conductor formed to couple bond pads 226A and 226B disposed on opposite sides of the substrate 202. Conductive material 218 may then be disposed within the openings of each tab 214 and 216 to couple the associated optical elements to respective bond pads 226A and 226B.

Figure 2C:
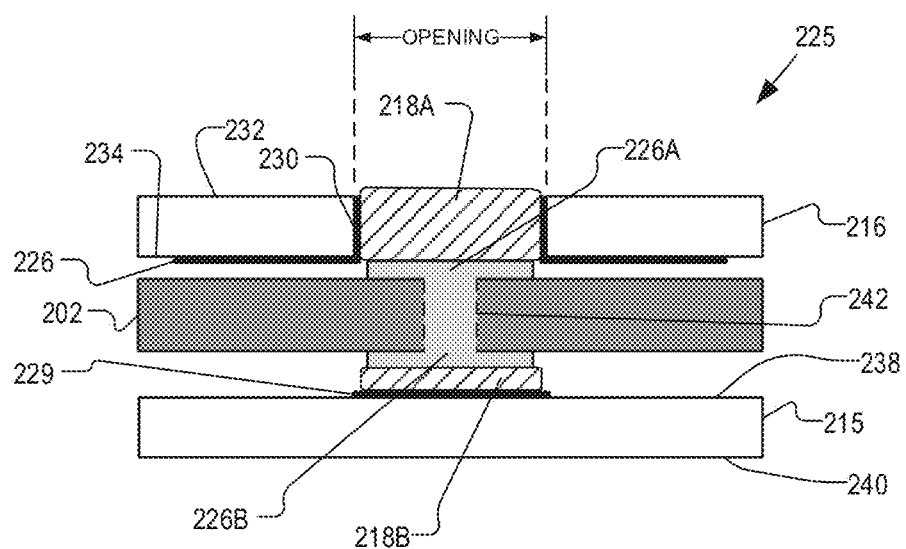
FIG. 2C is a cross-sectional view of an ophthalmic device in accordance with an embodiment of the present disclosure.

FIG. 2C is a cross-sectional view of an ophthalmic device 225 in accordance with an embodiment of the present disclosure. The ophthalmic device 225 may be an example of the ophthalmic devices 100 and/or 105. The ophthalmic device 225 may be similar to the ophthalmic device 205 except that an optical element 215 may not include an opening.

The illustrated embodiment of the ophthalmic device 225 includes the optical element 215, the substrate 202, and the optical element 216. The optical element 215 may be an example of the optical element 108 and/or 109. The optical element 215 may have a bond pad 229 disposed on a surface facing the substrate 202. The bond pad 229 may be formed on the surface of or partially recessed into the surface of the optical element 215, for example. The bond pad may be coupled by one or more conductive traces (not shown) to a transparent or semi-transparent conductor disposed in an optical area of the optical element 215.

Similar to the ophthalmic device 205, the via 242 may be formed through the substrate 202, which includes a conductor coupling bond pads 226A and 226B. The conductor coupling the bond pads 226A and 226B may be formed when one either or both of the bond pads 226A, B are formed, for example. One or both of the bond pads 226A, B may be coupled to control circuitry disposed on the substrate 202 via on or more electrical traces. The optical element 215 may be coupled to the bond pad 226B by the conductive material 218B. Additionally, the optical element 216 may be coupled to the bond pad 226A by the conductive material 218A. The conductive materials 218A and 218B may be formed from the same or different materials, which may be a conductive epoxy or silver paste, for example. The opening in the optical element 216 may provide a recess/cavity for receiving the conductive material 218A, for example. During fabrication, the conductive material 218A may be, at least partially, wicked into the recess/cavity to ensure electrical continuity between the bond pad 226A and the sidewall conductors 226. Additionally, the wicking of the conductive material 218A may provide a more aesthetically cleaner assembly of the ophthalmic device 225.

Figure 3:
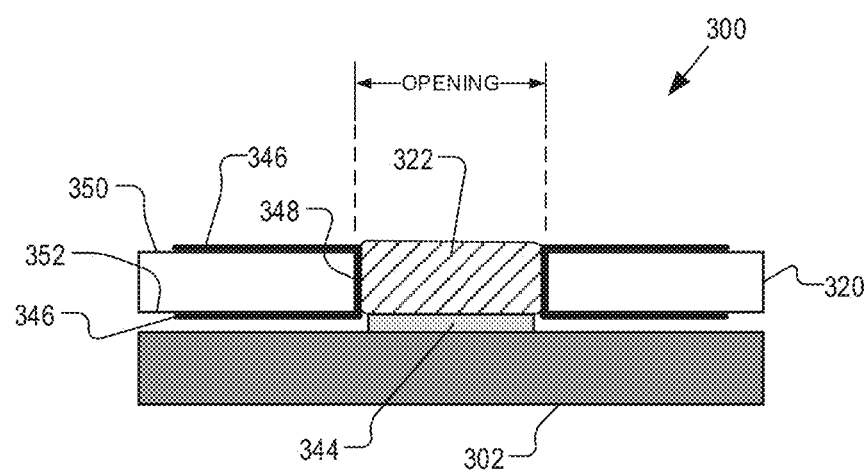
FIG. 3 is a cross-sectional view of an ophthalmic device including a patterned tab in accordance with an embodiment of the present disclosure.

FIG. 3 is a cross-sectional view of an ophthalmic device 300 including a patterned tab in accordance with an embodiment of the present disclosure. The ophthalmic device 300 may be an example of the ophthalmic device 100. The ophthalmic device 300 shows a cut-away through a tab of an optical element, such as the tab 120 of the second optical element 110.

The illustrated embodiment of the ophthalmic device 300 includes a substrate 302, a tab 320, and conductive material 322. The substrate 302, which may be an example of the substrate 102, may have a bond pad 344 disposed thereon. The bond pad, for example, may be formed from titanium and gold or aluminum. The tab 320, which may be part of an optical element, such as the second optical element 110, may have a conductor 346 disposed thereon. The conductor 346 may be disposed on a sidewall 348, an anterior side 350, and a posterior side 352. Additionally, the conductor 346 may couple to one or more transparent or semi-transparent conductors disposed in an optical area of the associated optical element body, for example.

Although the conductor 346 is shown to be one continuous film that wraps around the edges where the sides and sidewall intersect, the conductor 346 may be formed in multiple steps. For example, one or more metals may be deposited on each surface of the tab 320 in individual steps with overlap occurring at the edges to form a continuous film. The conductive material 322 may be disposed within an opening of the tab 320 and may be electrically coupled to the bond pad 344 and the conductor 348. The conductor 346 may be formed from one or more metals deposited on the various surfaces of the tab 320. For example, the conductor 346 may be formed from titanium and gold. Alternatively, the conductor 346 may be formed from silver or aluminum.

While the ophthalmic device depicts the substrate 302 adjacent to the posterior side 352 of the tab 320, an alternative configuration is contemplated by the disclosure. For example, the substrate 302 may have the bond pad 344 disposed on an opposite side, which may allow the substrate 302 to be adjacent to the anterior side 350.

Figure 4:
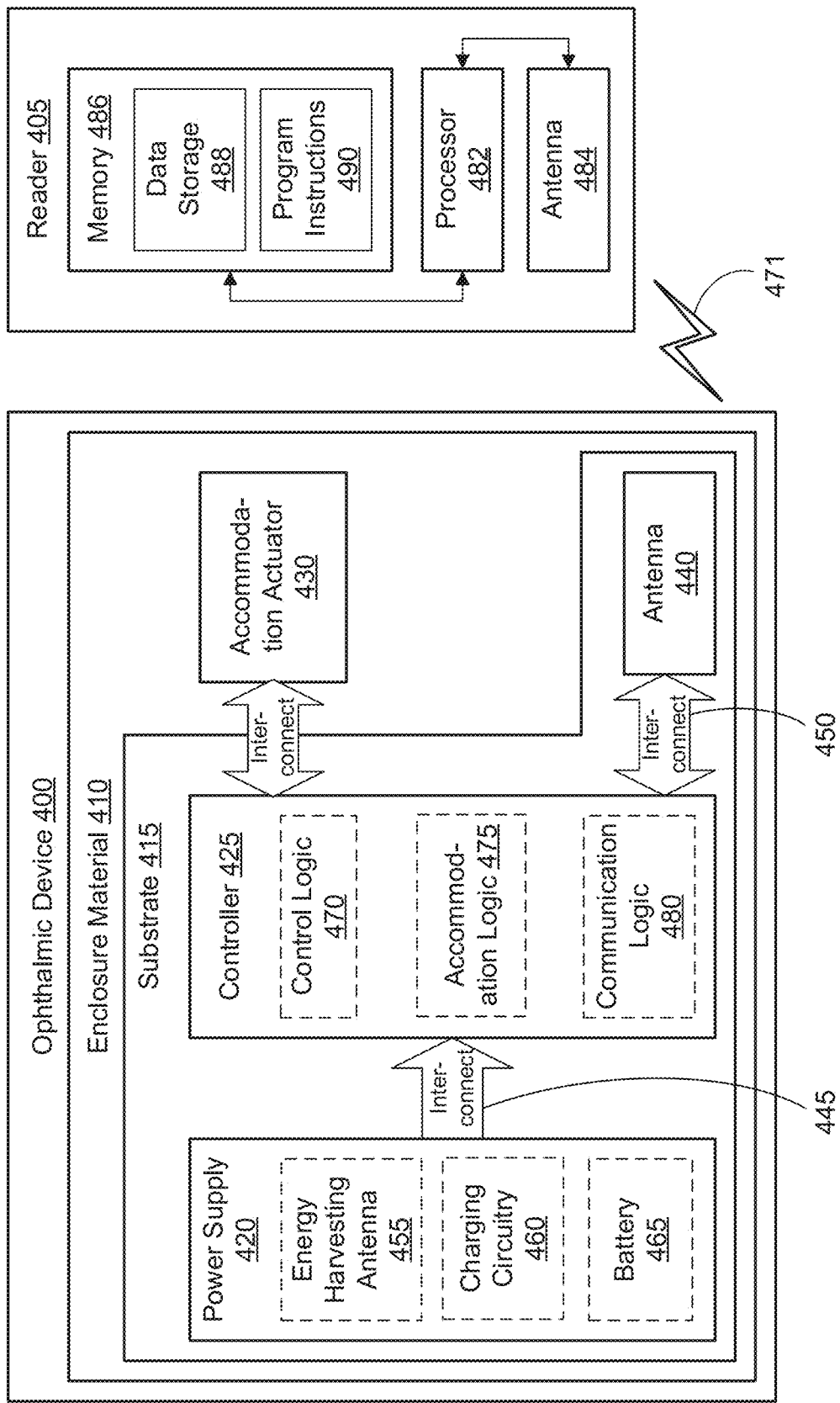
FIG. 4 is a functional block diagram of an ophthalmic device including patterned tabs in accordance with an embodiment of the present disclosure.

FIG. 4 is a functional block diagram of an ophthalmic device 400 including patterned tabs in accordance with an embodiment of the present disclosure. Ophthalmic device 400 may be an on-eye device, such as a contact lens or a smart contact lens, or an implantable device, such as an intraocular lens. In the depicted embodiment, ophthalmic device 400 includes an enclosure material 410 formed to be either contact-mounted to a corneal surface of an eye or implanted into an eye. A substrate 415 is embedded within or surrounded by enclosure material 410 to provide a mounting surface for a power supply 420, a controller 425, an antenna 440, and various interconnects 445 and 450. The substrate 415 and the associated electronics may be one implementation of the substrate 202 and the control electronics 104. The illustrated embodiment of power supply 420 includes an energy harvesting antenna 455, charging circuitry 460, and a battery 465. The illustrated embodiment of controller 425 includes control logic 470, accommodation logic 475, and communication logic 480. As shown, accommodation actuator 430 is disposed in the enclosure material 410.

Power supply 420 supplies operating voltages to the controller 425 and/or the accommodation actuator 430. Antenna 440 is operated by the controller 425 to communicate information to and/or from ophthalmic device 400. In the illustrated embodiment, antenna 440, controller 425, and power supply 420 are disposed on/in substrate 415, while accommodation actuator 430 is disposed in enclosure material 410 (not in/on substrate 415). However, in other embodiments, the various pieces of circuitry and devices contained in ophthalmic device 400 may be disposed in/on substrate 415 or in enclosure material 410, depending on the specific design of ophthalmic device 400. For example, in one embodiment, accommodation actuator 430 may be disposed on a transparent substrate.

Substrate 415 includes one or more surfaces suitable for mounting controller 425, power supply 420, and antenna 440. Substrate 415 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 415 to form circuitry, electrodes, etc. For example, antenna 440 can be formed by depositing a pattern of gold or another conductive material on substrate 415. Similarly, interconnects 445 and 450 can be formed by depositing suitable patterns of conductive materials on substrate 415. A combination of resists, masks, and deposition techniques can be employed to pattern materials on substrate 415. Substrate 415 can be a relatively rigid material, such as polyethylene terephthalate ("PET") or another material sufficient to structurally support the circuitry and/or electronics within enclosure material 410. Ophthalmic device 400 can alternatively be arranged with a group of unconnected substrates rather than a single substrate 415. For example, controller 425 and power supply 420 can be mounted to one substrate 415, while antenna 440 is mounted to another substrate 415 and the two can be electrically connected via interconnects. Substrate 415 may also be a continuous piece of semiconductor, housing all or some of the aforementioned pieces of device architecture as integrated circuitry.

Substrate 415 can be shaped as a flattened ring with a radial width dimension sufficient to provide a mounting platform for the embedded electronic components. Substrate 415 can have a thickness sufficiently small to allow substrate 415 to be embedded in enclosure material 410 without adversely influencing the profile of ophthalmic device 400. Substrate 415 can have a thickness sufficiently large to provide structural stability suitable for supporting the electronics mounted thereon. For example, substrate 415 can be shaped as a ring with a diameter of about 10 millimeters, a radial width of about 1 millimeter (e.g., an outer radius 1 millimeter larger than an inner radius), and a thickness of about 50 micrometers. Substrate 415 can optionally be aligned with the curvature of the eye-mounting surface of ophthalmic device 400 (e.g., convex surface). For example, substrate 415 can be shaped along the surface of an imaginary cone between two circular segments that define an inner radius and an outer radius. In such an example, the surface of substrate 415 along the surface of the imaginary cone defines an inclined surface that is approximately aligned with the curvature of the eye mounting surface at that radius.

In the illustrated embodiment, power supply 420 includes a battery 465 to power the various embedded electronics, including controller 425. Battery 465 may be inductively charged by charging circuitry 460 and energy harvesting antenna 455. In one embodiment, antenna 440 and energy harvesting antenna 455 are independent antennae, which serve their respective functions of energy harvesting and communications. In another embodiment, energy harvesting antenna 455 and antenna 440 are the same physical antenna that are time shared for their respective functions of inductive charging and wireless communications with reader 405. Additionally or alternatively, power supply 420 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 460 may include a rectifier/regulator to condition the captured energy for charging battery 465 or directly power controller 425 without battery 465. Charging circuitry 460 may also include one or more energy storage devices to mitigate high frequency variations in energy harvesting antenna 455. For example, one or more energy storage devices (e.g., a capacitor, an inductor, etc.) can be connected to function as a low-pass filter.

Controller 425 contains logic to choreograph the operation of the other embedded components. Control logic 470 controls the general operation of ophthalmic device 400, including providing a logical user interface, power control functionality, etc. Accommodation logic 475 includes logic for receiving signals from sensors monitoring the orientation of the eye, determining the current gaze direction or focal distance of the user, and manipulating accommodation actuator 430 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 480 provides communication protocols for wireless communication with reader 405 via antenna 440. In one embodiment, communication logic 480 provides backscatter communication via antenna 440 when in the presence of an electromagnetic field 471 output from reader 405. In one embodiment, communication logic 480 operates as a smart wireless radio-frequency identification ("RFID") tag that modulates the impedance of antenna 440 for backscatter wireless communications. The various logic modules of controller 425 may be implemented in software/firmware executed on a general purpose microprocessor, in hardware (e.g., application specific integrated circuit), or a combination of both.

Ophthalmic device 400 may include various other embedded electronics and logic modules. For example, a light source or pixel array may be included to provide visible feedback to the user. An accelerometer or gyroscope may be included to provide positional, rotational, directional or acceleration feedback information to controller 425.

The illustrated embodiment also includes reader 405 with a processor 482, an antenna 484, and memory 486. Memory 486 in reader 405 includes data storage 488 and program instructions 490. As shown reader 405 may be disposed outside of ophthalmic device 400, but may be placed in its proximity to charge ophthalmic device 400, send instructions to ophthalmic device 400, and/or extract data from ophthalmic device 400. In one embodiment, reader 405 may resemble a conventional contact lens holder that the user places ophthalmic device 400 in at night to charge, extract data, clean the lens, etc.

External reader 405 includes an antenna 484 (or group of more than one antennae) to send and receive wireless signals 471 to and from ophthalmic device 400. External reader 405 also includes a computing system with a processor 482 in communication with a memory 486. Memory 486 is a non-transitory computer-readable medium that can include, without limitation, magnetic disks, optical disks, organic memory, and/or any other volatile (e.g., RAM) or non-volatile (e.g., ROM) storage system readable by the processor 182. Memory 486 can include a data storage 488 to store indications of data, such as data logs (e.g., user logs), program settings (e.g., to adjust behavior of ophthalmic device 400 and/or external reader 405), etc. Memory 486 can also include program instructions 490 for execution by processor 482 to cause the external reader 405 to perform processes specified by the instructions 490. For example, program instructions 490 can cause external reader 405 to provide a user interface that allows for retrieving information communicated from ophthalmic device 400 or allows transmitting information to ophthalmic device 400 to program or otherwise select operational modes of ophthalmic device 400. External reader 105 can also include one or more hardware components for operating antenna 484 to send and receive wireless signals 471 to and from ophthalmic device 400.

External reader 405 can be a smart phone, digital assistant, or other portable computing device with wireless connectivity sufficient to provide the wireless communication link 471. External reader 405 can also be implemented as an antenna module that can be plugged into a portable computing device, such as in an embodiment where the communication link 471 operates at carrier frequencies not commonly employed in portable computing devices. In some instances, external reader 405 is a special-purpose device configured to be worn relatively near a wearer's eye to allow the wireless communication link 471 to operate with a low power budget. For example, the external reader 405 can be integrated in a piece of jewelry such as a necklace, earing, etc. or integrated in an article of clothing worn near the head, such as a hat, headband, etc.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device, comprising:
a plurality of optical elements arranged into a stack to form layers of a dynamic optic adapted to provide accommodation control, wherein a subset of optical elements of the plurality of optical elements each includes a tab extending radially outward from an edge perimeter of an optical element body portion, wherein the tab and the optical element body portion of a given one of the optical elements form a single member, wherein the optical element body portion of each of the optical elements extends across a center of the ophthalmic device and the optical element body portion of each of the optical elements overlap each other in the stack, and wherein each tab includes an opening formed through the tab; and
a substrate including a plurality of bond pads disposed on the substrate, wherein the bond pads are electrically conductive, wherein each optical element of the plurality of optical elements is coupled to one of the plurality of bond pads by a conductive material, and wherein the conductive material is disposed within respective openings of the subset of optical elements of the plurality of optical elements.

2. The ophthalmic device of claim 1, wherein a first conductor is at least disposed on sidewalls of the openings of the subset of optical elements, and wherein the conductive material is electrically coupled to the first conductor of each optical element of the subset of optical elements.

3. The ophthalmic device of claim 1, wherein a second conductor is disposed on at least one surface of at least one of the optical elements of the plurality of optical elements not part of the subset of optical elements, and wherein the conductive material couples the second conductor to one of the plurality of bond pads.

4. The ophthalmic device of claim 1, wherein a posterior optical element and an anterior optical element are coupled to the same bond pad, the anterior optical element included in the subset of optical elements.

5. The ophthalmic device of claim 4, wherein the posterior optical element does not include a tab.

6. The ophthalmic device of claim 1, wherein each of the plurality of optical elements includes a plurality of tabs.

7. The ophthalmic device of claim 1, wherein the conductive material is a conductive adhesive.

8. The ophthalmic device of claim 1, wherein the conductive material is silver paste.

9. The ophthalmic device of claim 1, wherein the substrate includes control electronics coupled to the plurality of bond pads.

10. The ophthalmic device of claim 1, wherein the dynamic optic further includes liquid crystal material disposed between adjacent ones of the plurality of optical elements and wherein the plurality of optical elements comprise transparent or semi-transparent conductors for applying a voltage across the liquid crystal material to change optical properties of the dynamic optic.

11. The ophthalmic device of claim 1, wherein each of the plurality of optical elements are formed into a hemi-spherical shell.

12. The ophthalmic device of claim 1, wherein each of the plurality of optical elements include transparent or semi-transparent conductors formed on at least one side, and coupled to the conductive material.

13. An ophthalmic device, comprising:
a first optical element having a first tab extending radially outward of a first perimeter edge of a first optical element body of the first optical element, wherein the first tab includes a first opening formed through the first tab and the first tab forms a single member with the first optical element body;
a second optical element having a second tab extending radially outward of a second perimeter edge of a second optical element body of the second optical element, wherein the second tab includes a second opening formed through the second tab and the second tab forms a single member with the second optical element body, wherein the first and second optical element bodies both extend across a center of the ophthalmic device and overlap each other in a stack;
a third optical element, wherein the first, second, and third optical elements are stacked to form a dynamic optic adapted to provide accommodation control; and
a substrate including at least two bond pads disposed on the substrate, wherein the first, second and third optical elements are each coupled to at least one of the two bond pads by a conductive material and wherein the at least two bond pads are electrically conductive.

14. The ophthalmic device of claim 13, wherein the first and third optical elements are coupled to the same bond pad.

15. The ophthalmic device of claim 13, wherein a first conductor disposed on sidewalls of the first and second openings is electrically coupled to the conductive material.

16. The ophthalmic device of claim 13, wherein a second conductor disposed on at least one surface of the third optical element is electrically coupled to the conductive material.

17. The ophthalmic device of claim 13, wherein the at least two bond pads are coupled to electronics disposed on the substrate via one or more conductive traces.

18. The ophthalmic device of claim 13, wherein the first optical element is an anterior optical element.

19. The ophthalmic device of claim 18, wherein the first optical element includes a transparent or semi-transparent conductive element disposed on a posterior side of the first optical element.

20. The ophthalmic device of claim 13, wherein the second optical element is a middle optical element.

21. The ophthalmic device of claim 20, wherein the second optical element includes a transparent or semi-transparent conductive element disposed on an anterior side and a posterior side of the second optical element.

22. The ophthalmic device of claim 13, wherein the third optical element is a posterior optical element.

23. The ophthalmic device of claim 22, wherein the third optical element includes a transparent or semi-transparent conductive element disposed on an anterior side of the third optical element.

24. The ophthalmic device of claim 1, wherein the substrate has an interior hole and the optical element body portion is disposed at least partially within, or extends at least partially across, the interior hole and the tab extends radially out from the optical element body portion to lap a portion of the substrate.

25. The ophthalmic device of claim 1, wherein the plurality of optical elements arranged into the stack to form layers of the dynamic optic comprise conductors, wherein the plurality of optical elements sandwich liquid crystal material between one or more adjacent ones of the optical elements in the stack, and wherein application of one or more voltages across the plurality of optical elements affects optical properties of the dynamic optic.

26. The ophthalmic device of claim 1, wherein the tab and the optical element body portion of the given one of the optical elements forming the single member are formed of a common material.

\* \* \* \* \*